(12) United States Patent
Sieweke

(10) Patent No.: US 9,175,265 B2
(45) Date of Patent: Nov. 3, 2015

(54) METHOD FOR INDUCING EXTENDED SELF-RENEWAL OF FUNCTIONALLY DIFFERENTIATED SOMATIC CELLS

(75) Inventor: Michael Sieweke, Marseille Cedex (FR)

(73) Assignees: Institut National de la Sante et de la Recherche Medicale (INSERM), Paris (FR); Centre National de la Recherche Scientifique (CNRS), Paris (FR); Universite de la Mediterranee (Aix-Marseille II), Marseilles (FR)

( * ) Notice: Subject to any disclaimer, the term of this patent is extended or adjusted under 35 U.S.C. 154(b) by 0 days.

(21) Appl. No.: 13/382,724

(22) PCT Filed: Jul. 8, 2010

(86) PCT No.: PCT/EP2010/059843
§ 371 (c)(1),
(2), (4) Date: Mar. 9, 2012

(87) PCT Pub. No.: WO2011/003988
PCT Pub. Date: Jan. 13, 2011

(65) Prior Publication Data
US 2012/0156179 A1 Jun. 21, 2012

(30) Foreign Application Priority Data
Jul. 8, 2009 (EP) .................... 09305661

(51) Int. Cl.
| | | |
|---|---|---|
| *C12N 5/00* | (2006.01) | |
| *C12N 15/00* | (2006.01) | |
| *C12N 15/63* | (2006.01) | |
| *A61K 48/00* | (2006.01) | |
| *C07H 21/04* | (2006.01) | |
| *C12N 5/0786* | (2010.01) | |
| *C12N 5/0781* | (2010.01) | |
| *C12N 15/85* | (2006.01) | |
| *C12N 15/86* | (2006.01) | |
| *C12N 15/90* | (2006.01) | |
| *C12N 5/078* | (2010.01) | |
| *A61K 35/12* | (2015.01) | |

(52) U.S. Cl.
CPC ............ *C12N 5/0645* (2013.01); *C12N 5/0635* (2013.01); *C12N 5/0641* (2013.01); *A61K 35/12* (2013.01); *C07H 21/04* (2013.01); *C12N 5/0634* (2013.01); *C12N 15/63* (2013.01); *C12N 15/85* (2013.01); *C12N 15/86* (2013.01); *C12N 15/907* (2013.01); *C12N 2501/60* (2013.01); *C12N 2510/00* (2013.01); *C12N 2517/02* (2013.01)

(58) Field of Classification Search
CPC ...... C12N 5/0634; C12N 15/63; C12N 15/85; C12N 15/86; C07H 21/04
USPC .................... 435/320.1, 375, 455; 424/93.21; 536/23.5
See application file for complete search history.

(56) References Cited

FOREIGN PATENT DOCUMENTS

| | | |
|---|---|---|
| WO | 2008/084069 | 7/2008 |
| WO | 2009/032456 | 3/2009 |

OTHER PUBLICATIONS

Sakurada et al., 2011, US 20110039332 A1, effective filed, Nov. 20, 2007.*
Gorecki, D., 2001, Expert Opin. Emerging Drugs, 6(2): 187-198.*
Bennett, J., 2003, Gene Therapy, vol. 10, p. 977-982.*
Thomas et al., 2003, Nature Reviews/ Genetics, vol. 4, p. 346-358.*
Lebedeva et al., 2003, Seminars in Cancer Biology, vol. 12, p. 169-178.*
Kodama et al., 2006, Current Medicinal Chemistry, vol. 13, p. 2155-2161.*
Hurlin, Peter, 2005, Birth Defect Research (Part C), vol. 75, p. 340-352.*
Pearson et al., 2008, The International Journal of Biochemistry & Cell Biology, vol. 40, p. 1996-2001.*
Brey et al., 2009, International Journal of Biological Sciences, vol. 5, No. 6, p. 622-636.*
Skolnick et al., 2000, Trends in Biotech, vol. 18, p. 34-39.*
Tomasinsig et al., 2005, Current Protein and Peptide Science, vol. 6, p. 23-34.*
Smallwood et al., 2002, Virology, vol. 304, p. 135-145.*
Chattopadhyay et al., 2004, Virus Research, vol. 99, p. 139-145.*
Sun et al., 2006, Critical Reviews in Eukaryotic Gene Expression, vol. 16, No. 3, p. 211-231.*
Nguyen et al., 2010, Advanced Drug Delivery reviews, vol. 62, p. 1175-1186.*
Aziz et al., 2009, Science, vol. 326, p. 867-871.*
N. Maherali et al.; "Directly Reprogrammed Fibroblasts Show Global Epigenetic Remodeling and Widespread Tissue Contribution"; Cell Stem Cell, vol. 1, Jul. 2007, pp. 55-70.
C. A. Lyssiotis et al.; "Reprogramming of Murine Fibroblasts to Induced Pluripotent Stem Cells with Chemical Complementation of Klf4"; Proceedings of the National Academy of Sciences of the United States (PNAS), vol. 106, No. 22; Jun. 2, 2009; pp. 8912-8917.
H. Niwa; "Self-Renewal of Pluripotent Embryonic Stem Cells is Mediated Via Activation of STAT3"; Genes & Development, vol. 12, No. 13; Jul. 1, 1998; pp. 2048-2060.
Blasi et al.; "Selective Immortalization of Murine Macrophages From Fresh Bone Marrow by a raf/myc Recombinant Murine Retrovirus"; Nature, vol. 318, No. 6047, pp. 667-670.

* cited by examiner

*Primary Examiner* — Shin Lin Chen
(74) *Attorney, Agent, or Firm* — Whitham, Curtis, Christofferson & Cook, P.C.

(57) ABSTRACT

Mouse or human hematopoietic cells are transduced in vitro with one or more vectors encoding c-Myc and Klf4 genes, to overexpress both c-Myc and Klf4. The transduced cells produce self-renewing populations of macrophages, monocytes, monocyte-derived macrophages, B lymphocytes or erythroid cells. The self-renewing cell populations may include a pharmaceutical composition.

8 Claims, No Drawings

METHOD FOR INDUCING EXTENDED SELF-RENEWAL OF FUNCTIONALLY DIFFERENTIATED SOMATIC CELLS

FIELD OF THE INVENTION

The present invention relates to a method for inducing extended self-renewal of functionally differentiated somatic cells comprising a step of activating expression of a Myc family gene and a Klf family gene in said cells or contacting said cells with a Myc family protein and a Klf family protein.

BACKGROUND OF THE INVENTION

For several years, technologies in the field of regenerative medicine have focussed on stem cells notably pluripotent stem cells (such as embryonic stem cells and more recently induced pluripotent stem cells), as these cells have the capacity to self-renew and to differentiate into multiple specialized cell types. The concept of regenerative medicine involves transplanting cells of interest with the goal of repairing and regenerating a target tissue and/or target organ which cannot regenerate itself, since most tissues or organs, such as heart tissue and neural tissue, are essentially composed of functionally differentiated somatic cells and cannot regenerate alone or, at least, cannot regenerate efficiently, due to their very limited capacity of self-renewal.

Indeed, in metazoan organisms terminal differentiation is generally tightly linked to cell cycle exit, whereas the undifferentiated state of pluripotent stem cells is associated with unlimited self-renewal. The non-proliferative state of terminally differentiated cells is notably assured by robust, often redundant mechanisms and in rare exceptions where fully mature cells can re-enter the cycle, proliferation remains transient and usually involves de-differentiation. It remains unknown what renders differentiated cells refractory to the very mitogen signals that stimulate the proliferation of their direct precursors. For example, the proliferative response of myelo-monocytic progenitors to M-CSF is lost upon differentiation to macrophages, despite the continued ability of these mature cells to sense the cytokine. Consequently, myeloid progenitor cells form colonies in semi-solid M-CSF containing medium, whereas blood monocytes and tissue macrophages do not.

However, international patent application WO 2008/084069 recently discloses a method for generating, maintaining and expanding monocytes and macrophages in long term culture by inhibiting the expression or the activity of MafB and c-Maf in said cells; and expanding the cells in the presence of at least one cytokine, such as M-CSF.

Now, the inventors have underlined that such method is based on a mechanism that depends on regulated activation of c-Myc and Klf4 and have surprisingly demonstrated that long term proliferating cells thus obtained are not tumorigenic despite the fact that c-Myc and Klf4 are both oncogenes as described in Rowland et al. 2006 and Adhikary et al. 2005.

SUMMARY OF THE INVENTION

Therefore, a first aspect of the invention relates to a method for inducing extended self-renewal of functionally differentiated somatic cells comprising a step of activating expression of a Myc family gene and a Klf family gene in said cells.

A second aspect of the invention relates to a method for inducing extended self-renewal of functionally differentiated somatic cells comprising a step of contacting said cells with a Myc family protein and a Klf family protein.

A third aspect of the invention relates to a combination of a Myc family member (gene or protein) and a Klf family member (gene or protein) for use in a method for inducing extended self-renewal of functionally differentiated somatic cells.

The invention also relates a kit comprising a Myc family member (gene or protein) and a Klf family member (gene or protein) for use in a method for inducing extended self-renewal of functionally differentiated somatic cells.

The invention also relates to the use of a Myc family gene or protein and a Klf family gene or protein for inducing extended self-renewal of functionally differentiated somatic cells.

The invention further relates to a population of functionally differentiated somatic cells obtainable by the method of the invention and a pharmaceutical composition comprising such population and a pharmaceutically acceptable carrier or excipient.

DETAILED DESCRIPTION OF THE INVENTION

The inventors have thus demonstrated that it was possible to obtain functionally differentiated somatic cells in large quantity without passing through pluri- or multi-potent stem cell intermediates and without malignant transformation by inducing the extended self-renewal of said functionally differentiated somatic cells by activating expression of c-Myc and Klf4 in said cells. The inventors have indeed shown that said functionally differentiated somatic cells may proliferate in long term cultures but are also non-tumorigenic, notably after transplantation into mice.

Therefore, a first aspect of the invention relates to a method for inducing extended self-renewal of functionally differentiated somatic cells comprising a step of activating expression of a Myc family gene and a Klf family gene in said cells.

In a particular embodiment, the method according to the invention is an in vitro method for inducing extended self-renewal of functionally differentiated somatic cells comprising a step of activating expression of a Myc family gene and a Klf family gene in said cells.

As used herein, the term "Myc family gene" refers to any gene selected from the group consisting of c-Myc, N-Myc, L-Myc and S-Myc. Such genes have their generally recognized meaning in the art and were described in reference (Adhikary et al. 2005). The Myc family gene can be from any source, but typically is a mammalian (e.g., human and non-human primate, or rodent) Myc family gene. In a particular embodiment, the Myc family gene is c-Myc also called myelocytomatosis oncogene. The amino acid sequences and nucleotide sequences of Myc family genes are known per se for the skilled man in the art and are publically available in the NCBI Genbank. For example, the naturally occurring human c-Myc gene has a nucleotide sequence shown in Genbank Accession number NM_002467 and the naturally occurring human protein has an aminoacid sequence shown in Genbank Accession number NP_002458.

As used herein, the term "Klf family gene" refers to any gene selected from the group consisting of Klf1, Klf2, Klf3, Klf4, Klf5, Klf6, Klf8, Klf9, Klf10, Klf11, Klf12, Klf13, Klf14, Klf15, Klf16, and Klf17. Such genes have their generally recognized meaning in the art. The Klf family gene can be from any source, but typically is a mammalian (e.g., human and non-human primate, or rodent) Klf family gene. In a particular embodiment, the Klf family gene is Klf4 also called Kruppel-like factor 4. The amino acid sequences and nucleotide sequences of Klf family genes are known per se for the skilled man in the art and are publically available in the NCBI Genbank. For example, the naturally occurring human Klf4 gene has a nucleotide sequence shown in Genbank Accession number NM_004235 and the naturally occurring human protein has an amino acid sequence shown in Genbank Accession number NP_004226.

As used herein, references to specific genes (e.g., c-Myc or Klf4 genes) can include a nucleic acid having a native (endogenous) polynucleotide sequence, in particular the human gene, or any allelic or polymorphic variant thereof, as well as the orthologous sequences found in other species. Polynucleotide variants may contain one or more substitutions, additions, deletions and/or insertions. For example, due to the inherent degeneracy of the genetic code, other DNA sequences that encode substantially the same or a functionally equivalent amino acid sequence may be produced and these sequences may be used to clone and express a given polypeptide.

As will be recognized by the skilled artisan, polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

As used herein, the terms "DNA" and "polynucleotide" and "nucleic acid" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As used herein, references to specific proteins (e.g., c-Myc or Klf4 proteins) can include a polypeptide having a native amino acid sequence, as well as variants and modified forms regardless of their origin or mode of preparation. A protein that has a native amino acid sequence is a protein having the same amino acid sequence as obtained from nature (e.g., a naturally occurring c-Myc or Klf4). Such native sequence proteins can be isolated from nature or can be prepared using standard recombinant and/or synthetic methods. Native sequence proteins specifically encompass naturally occurring truncated or soluble forms, naturally occurring variant forms naturally occurring allelic variants and forms including post-translational modifications. A native sequence protein includes proteins following post-translational modifications such as glycosylation, or phosphorylation, ubiquitination, sumoylation or other modifications of some amino acid residues.

Variants refer to proteins that are functional equivalents to a native sequence protein that have similar amino acid sequences and retain, to some extent, one or more activities of the native protein. Variants also include fragments that retain activity. Variants also include proteins that are substantially identical (e.g., that have 80, 85, 90, 95, 97, 98, 99%, sequence identity) to a native sequence. Such variants include proteins having amino acid alterations such as deletions, insertions and/or substitutions. A "deletion" refers to the absence of one or more amino acid residues in the related protein. The term "insertion" refers to the addition of one or more amino acids in the related protein. A "substitution" refers to the replacement of one or more amino acid residues by another amino acid residue in the polypeptide. Typically, such alterations are conservative in nature such that the activity of the variant protein is substantially similar to a native sequence protein. In the case of substitutions, the amino acid replacing another amino acid usually has similar structural and/or chemical properties. Insertions and deletions are typically in the range of 1 to 5 amino acids, although depending upon the location of the insertion, more amino acids can be inserted or removed.

In a particular embodiment, the present invention relates to a method for inducing extended self-renewal of functionally differentiated somatic cells comprising a step of activating expression of c-Myc gene and a Klf4 gene in said cells.

In another particular embodiment, the Myc family gene is c-Myc and the Klf family gene is Klf2.

In another particular embodiment, the Myc family gene is c-Myc and the Klf family gene is Klf5.

In another particular embodiment, the Myc family gene is N-Myc and the Klf family gene is Klf4.

In another particular embodiment, the Myc family gene is N-Myc and the Klf family gene is Klf2.

In still another particular embodiment, the Myc family gene is N-Myc and the Klf family gene is Klf5.

As used herein, the term "functionally differentiated somatic cells" refers to cells specialized for a particular function (e.g., lymphocytes, neurons or muscle cells). It must be further noted that most tissues or organs cannot, or at least cannot efficiently, regenerate. Indeed, such tissues or organs are composed of differentiated cells that are incapable of making identical copies of themselves (self-renewal) for the lifetime of the organism. Thus, in certain embodiments of the invention, functionally differentiated cells of interest are cells that cannot self-renew or cannot self-renew efficiently themselves or for which replacement from adult tissue stem or progenitor cells is very rare or inefficient. Functionally differentiated somatic cells of the present invention are typically from mammalian origin, such as for example, human, primate, horse, bovine, camel, ovine, dog, cat, rat or mouse.

For example, the functionally differentiated somatic cells are selected in the group consisting of epidermal cells, epithelial cells, keratinocytes, neurons (including motorneurons, specific neurotransmitter producing neurons such as dopaminergic neurons), glia cells, retinal cells, lens cells of the cornea, hair cells of the inner ear, chondrocytes, chondroblasts, endocrine pancreatic cells (including pancreatic beta cells), hepatocytes, endothelial cells, hematopoietic cells (including erythrocytes, lymphocytes (including B, T and NK lymphocytes), monocytes, macrophages and dendritic cells), muscle cells such as cardiomyocytes, skeletal myocytes and other muscle cells, osteoblasts and osteoclasts. These examples are illustrative rather than limiting.

In an embodiment, the functionally differentiated somatic cells are hematopoietic cells.

In a particular embodiment, the functionally differentiated somatic cells are monocytes, macrophages or dendritic cells.

In another particular embodiment, the functionally differentiated somatic cells are B and T lymphocytes.

In another particular embodiment, the functionally differentiated somatic cells are thrombocytes.

In still another particular embodiment, the functionally differentiated somatic cells are erythrocytes.

In another embodiment, the functionally differentiated somatic cells are selected in the group consisting of cardiomyocytes, hepatocytes and adipocytes.

It should be noted that the Klf family gene for which the expression is activated may be chosen depending on the related functionally differentiated somatic cells. Indeed a given functionally differentiated somatic cells shows a specific expression regarding the Klf genes as described in Pearson et al. 2008.

Typically, when the functionally differentiated somatic cells are cardiomyocytes, the Klf family gene for which the expression is activated may be selected from the group consisting of Klf2, Klf5, Klf6, Klf10, Klf13 and Klf15.

In a particular embodiment, when the functionally differentiated somatic cells are cardiomyocytes the Klf family gene may be selected from the group consisting of Klf5, Klf10, Klf13 and Klf15 as described in Haldar et al. 2007.

Typically, when the somatic cells are skeletal myocytes, the Klf family gene for which the expression is activated may be selected from the group consisting of Klf6, Klf13 and Klf15.

Typically when the somatic cells are adipocytes, the Klf family gene for which the expression is activated may be selected from the group consisting of Klf2, Klf5 and Klf15.

Typically when the somatic cells are neurons, the Klf family gene for which the expression is activated may be selected from the group consisting of Klf6, Klf7 and Klf9.

Typically when the somatic cells are osteoblasts, the Klf family gene may be Klf10.

Typically when the somatic cells are erythroid cells, the Klf family gene for which the expression is activated may be selected from the group consisting of Klf1, Klf2, Klf6 and Klf1.

Typically when the somatic cells are T-lymphocytes, the Klf family gene for which the expression is activated may be selected from the group consisting of Klf2, Klf4 and Klf13.

Typically when the somatic cells are hepatocytes, the Klf family gene may be Klf6.

Typically when the somatic cells are endothelial cells, the Klf family gene may be Klf5.

Typically when the somatic cells are keratinocytes, the Klf family gene may be Klf4.

It should be further noted that this selection of KLF members is based on the current published literature and should be seen as illustrative rather than limitative.

According to one embodiment, genetic material encoding a Myc family gene and a Klf family gene can be introduced by transfection or transduction into the somatic cells using a vector, such as an integrating- or non-integrating vector. After introduction, the DNA segment(s) encoding the Myc family gene and Klf family gene can be located extra-chromosomally (e.g., on an episomal plasmid) or stably integrated into cellular chromosome(s). As used herein, the term "vector" refers to a nucleic acid molecule capable of transporting another nucleic acid to which it has been linked into a host cell in vitro, in vivo or ex vivo. Such vectors may comprise regulatory elements, such as a promoter, enhancer, terminator and the like, to cause or direct expression of said polypeptide upon administration to a subject. The promoter region may be homologous or heterologous with respect to the coding sequence, and provide for ubiquitous, constitutive, regulated and/or tissue specific expression, in any appropriate host cell, including for in vivo use. Examples of promoters include bacterial promoters (T7, pTAC, Trp promoter, etc.), viral promoters (LTR, TK, CMV-IE, etc.), mammalian gene promoters (albumin, PGK, etc), and the like. The vector can include a single DNA segment encoding a Myc family gene or a Klf family gene or the both. The vectors may further comprise one or several origins of replication. The vector can optionally encode a selectable marker to identify cells that have taken up and express the vector. As an example, when the vector confers antibiotic resistance on the cells, antibiotic can be added to the culture medium to identify successful introduction of the vector into the cells. As used herein, the term "viral vector" refers to a modified virus particle which can be used to introduce a nucleic acid molecule and/or a peptide or other molecule into a target cell.

Examples of viral vector include retrovirus, adenovirus, parvovirus (e.g. adeno-associated viruses or AAV vectors), coronavirus, negative strand RNA viruses such as ortho-myxovirus (e.g., influenza virus), rhabdovirus (e.g., rabies and vesicular stomatitis virus), paramyxovirus (e.g. measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus.

Such recombinant viruses may be produced by techniques known in the art, such as by transfecting packaging cells or by transient transfection with helper plasmids or viruses. The vectors described herein can be constructed and engineered using art-recognized techniques to increase their safety for use in therapy and to include suitable expression elements and genes of interest. Standard techniques for the construction of expression vectors suitable for use in the present invention are well-known to one of ordinary skill in the art and can be found in such publications such as Sambrook J, et al, "Molecular cloning: a laboratory manual," (3rd ed. Cold Spring Harbor Press, Cold Spring Harbor, N.Y. 2001), incorporated herein by reference as if set forth in its entirety.

Thus, in one particular embodiment, a vector encoding a Myc family gene and/or a Myc family gene is used.

In one particular embodiment, the vector is a viral vector.

In one particular embodiment, the viral vector is a retroviral vector. Retroviral vectors are transduced by packaging the vectors into virions prior to contact with a cell.

According to this embodiment, the viral vector is preferably a lentiviral vector.

In another embodiment, the viral vector is an adenoviral vector.

In another particular embodiment, the vector is a non-viral vector.

In another particular embodiment, the non-viral vector is an episomal vector.

In a further particular embodiment, the episomal vector is a plasmid.

References herein to a "non-viral" vector indicate that the vector cannot encode an infectious virus. Accordingly, such non-viral vector refers to a vector which does not encode all or part of a viral genome sufficient to give rise to an infectious or replication-competent virus, although such vector can contain structural elements obtained from one or more virus.

It should be further noted that both the transgenes (i.e. a Myc family gene and a Klf family gene) may be provided on a single vector (viral or non-viral).

For instance, one strong, constitutive transcriptional promoter may provide transcriptional control for both the transgenes, which may be provided as an expression cassette. Separate expression cassettes on a vector may be under the transcriptional control of separate strong, constitutive promoters, which may be copies of the same promoter or may be distinct promoters. Various heterologous promoters are known in the art and may be used depending on transgenes such as the desired expression level of the transgenes.

The invention also encompasses use of gene delivery systems comprising a nucleic acid molecule and a non-viral gene delivery vehicle. Examples of non viral gene delivery vehicles include liposomes and polymers such as polyethylenimines, cyclodextrins, histidine/lysine (HK) polymers, etc.

A second aspect of the invention relates to a method for inducing extended self-renewal of functionally differentiated somatic cells comprising a step of contacting said cells with a Myc family protein and a Klf family protein.

In one embodiment, a Myc family protein and a Klf family protein or variants thereof may be introduced to the target cell by means of any procedure known for the delivery of proteins to cells, ex vivo, on cells in culture or removed from a subject, or in vivo.

In a particular embodiment, the method according to the invention is an in vitro method for inducing extended self-renewal of functionally differentiated somatic cells comprising a step of contacting said cells with a Myc family protein and a Klf family protein.

In a particular embodiment, the Myc family protein is c-Myc and the Klf family protein is Klf4.

In another particular embodiment, the Myc family gene is c-Myc and the Klf family gene is Klf2.

In another particular embodiment, the Myc family gene is c-Myc and the Klf family gene is Klf5.

In another particular embodiment, the Myc family gene is N-Myc and the Klf family gene is Klf4.

In another particular embodiment, the Myc family gene is N-Myc and the Klf family gene is Klf2.

In still another particular embodiment, the Myc family gene is N-Myc and the Klf family gene is Klf5.

As previously mentioned, the Klf family gene for which the expression is activated may be chosen depending on the related functionally differentiated somatic cells.

The delivery of protein is the process by which a protein crosses the cell plasma membrane. Traditionally, methods to introduce proteins into cells include micro-injection, electroporation and nanoparticles for protein drug delivery.

A number of protein-transduction domains (PTDs) have also been developed that mediate protein delivery into cells. These PTDs or signal peptide sequences are naturally occurring polypeptides of 15 to 30 amino acids, which normally mediate protein secretion in the cells. They are composed of a positively charged amino terminus, a central hydrophobic core and a carboxyl-terminal cleavage site recognized by a signal peptidase. Examples of such membrane-transducing peptides include Trojan peptides, human immunodeficiency virus (HIV)-1 transcriptional activator (TAT) protein or its functional domain peptides, and other peptides containing protein-transduction domains (PTDs) derived from translocation proteins such as *Drosophilia* homeotic transcription factor Antennapedia (Antp) and herpes simplex virus DNA-binding protein, VP22, and the like. Some commercially available peptides, for example, penetratin 1, Pep-1 (Chariot reagent, Active Motif Inc., CA) and HIV GP41 fragment (519-541), can be used for protein delivery.

Recently, the use of lipid liposomes or the like that can complex with a protein of interest and promote the delivery of the protein into the cell has also been demonstrated. Products available commercially can be used, such as BioPORTER (Gene Therapy Systems), or ProVectin (Imgenex, San Diego, Calif.).

The above methods do not limit the scope of the invention and it is to be understood that the one skilled in the art may readily make use of any other known appropriate methods for delivering a protein to a cell in vivo or in vitro.

Alternatively, biological or chemical compounds mimicking a Myc family protein and a Klf family protein activity may be used for inducing extended self-renewal of functionally differentiated somatic cells. In a particular embodiment, such biological or chemical compounds mimic c-Myc and Klf4 protein activity.

Therefore, the invention also relates to a method for inducing extended self-renewal of functionally differentiated somatic cells comprising a step of contacting said cells with a biological or a chemical compound mimicking a Myc family protein and a biological or a chemical compound mimicking a Klf family protein.

In a particular embodiment, said method is an in vitro method for inducing extended self-renewal of functionally differentiated somatic cells comprising a step of contacting said cells with a biological or a chemical compound mimicking a Myc family protein and a biological or chemical compound mimicking a Klf family protein.

Accordingly, a chemical compound belonging to the paullones structural class may be used in replacement of Klf4 as described in Lyssiotis et al. 2010.

In one embodiment, such chemical compounds belonging to the paullone structural class are described in the international Patent Application WO 99/65910 and have the following formula:

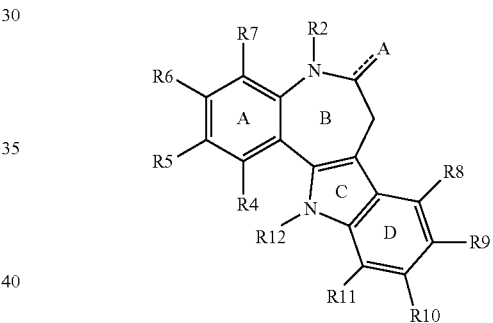

wherein A is oxygen or sulfur coupled to the right by a single or double bond; R2 is selected from the group consisting of hydrogen, aryl, lower aliphatic substituents, particularly alkyl and lower alkyl ester; R4-R7 are independently selected from the group consisting of alkoxy, amino, acyl, aliphatic substituents, particularly alkyl, alkenyl and alkinyl substituents, aliphatic alcohols, particularly alkyl alcohols, aliphatic nitriles, particularly alkyl nitriles, cyano, nitro, carboxyl, halogen, hydrogen, hydroxyl, imino, and $\alpha,\beta$ unsaturated ketones; R8-R11 are independently selected from the group consisting of aliphatic substituents, particularly alkyl, alkenyl and alkinyl substituents, particularly lower aliphatic substituents, aliphatic alcohols, particularly alkyl alcohols, alkoxy, acyl, cyano, nitro, epoxy, haloalkyl groups, halogen, hydrogen and hydroxyl; R12 is selected from the group consisting of aliphatic groups, particularly lower alkyl groups, aliphatic alcohols, particularly alkyl alcohols, carboxylic acids and hydrogen.

In a particular embodiment, the chemical compound belonging to the paullone structural class is the kenpaullone or 9-Bromo-7,12-dihydro-indolo[3,2-d][1]benzazepin-6 (5H)-one, having the following formula:

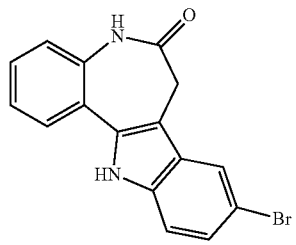 [SMILES: O=C1Cc2c([nH]c3ccc(Br)cc23)-c2ccccc2N1]

Alternatively, other chemical structural compounds may be used in replacement of Klf4 such as flavones and lysergamides as also described in Lyssiotis et al. 2010.

Accordingly, in another embodiment, a chemical compound belonging to the flavone structural class may be used in replacement of Klf4.

In a particular embodiment, the chemical compound belonging to the flavone structural class is the 7-hydroxyflavone, having the following formula:

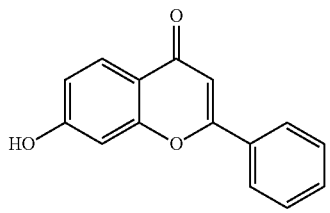 [SMILES: O=c1cc(-c2ccccc2)oc2cc(O)ccc12]

In another embodiment, a chemical compound belonging to the lysergamide structural class may be used in replacement of Klf4.

In a particular embodiment, the chemical compound belonging to the lysergamide structural class is the lysergic acid ethylamide, having the following formula:

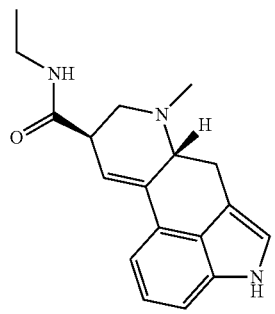 [SMILES: CCNC(=O)[C@@H]1C=C2c3cccc4[nH]cc(c34)C[C@H]2N(C)C1]

In still another embodiment, a biological or a chemical compound activating the Wnt pathway signaling may be used in replacement of c-Myc.

Accordingly, in one embodiment, the chemical compound activating the Wnt pathway signaling may be a Wnt agonist.

In a particular embodiment, the Wnt agonist is the protein Wnt3a as described in Marson et al. 2009 and the international publication WO 2009/032194.

In a still particular embodiment, the Wnt agonist is a chemical compound belonging to the 5-thiophenepyrimidine class as described in Wang et al. 2009 and in the international patent application WO 2010/056907, having the following formula:

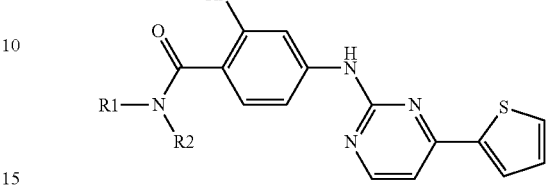

wherein: R1 is selected from hydrogen and C1-6alkyl; R2 is selected from C1-6alkyl and X1NR4R5; wherein X1 is C1-4alkylene; R4 and R5 are independently selected from hydrogen and C1-4alkyl; or R4 and R5 together with the nitrogen to which they are both attached, and optionally with another heteroatom chosen from the group O, S and N, form a 6 member heterocycle containing 1 to 2 heteroatoms; or R1 and R2 together with the nitrogen to which they are both attached, and optionally with another heteroatom chosen from the group O, S and N, form a 6 member heterocycle containing 1 to 2 heteroatoms; wherein said heterocycle formed from R1 and R2 or R4 and R5 can be optionally substituted with C1-4alkyl; and R3 is selected from hydrogen, halo, C1-4alkyl, halo-substituted-C1-4alkyl, C1-4alkoxy and halo-substituted-C1-4alkoxy.

In a particular embodiment, the chemical compound belonging to the 5-thiophenepyrimidine class is the 2-chloro-N-(2-morpholinoethyl)-4-(4-(thiophen-2-yl)pyrimidin-2-ylamino)benzamide having the following formula:

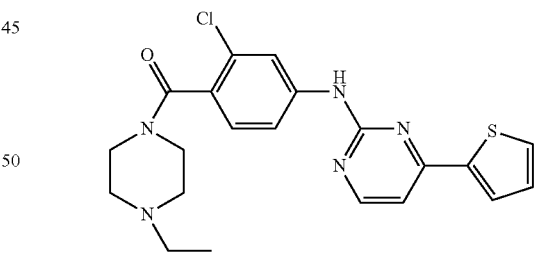

In another particular embodiment, the Wnt agonist is a chemical compound belonging to the aminopyridine class as described in Wang et al. 2009.

In still another particular embodiment, the Wnt agonist is a chemical compound belonging to the indirubin structural class as described in Wang et al. 2009.

Accordingly, such chemical compounds belonging to the indirubin class are described in the international Patent Application WO 2005/041954. Such compounds comprise an indirubin molecule substituted with a halogen at position C6 of the indirubin molecule.

In a particular embodiment, said compound belonging to the indirubin structural class is the 6-bromoindirubin-3'-oxime ("BIO") having the following formula:

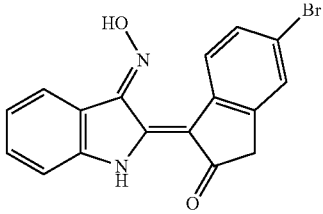 [SMILES: O=C1Cc2cc(Br)ccc2/C1=C1/Nc2ccccc2/C1=N\O]

Other substituted indirubins which may be used are 3'-,7-substituted indirubins as described in the international Patent Application WO 2007/099402 or 3'-,6-substituted indirubins as described in the international Patent Application WO 2010/013168.

In another embodiment, a chemical compound activating the Wnt pathway signalling may be a glycogen synthase kinase 3 (GSK3) inhibitor.

Reference to GSK3 inhibition refers to inhibition of one or more GSK3 enzymes. The family of GSK3 enzymes is well-known in the art. In specific embodiments GSK3-β is inhibited. GSK3α inhibitors are also suitable, and in general inhibitors for use in the invention inhibit both. A wide range of GSK3 inhibitors are known, by way of example, the inhibitors CHIR 98014, AR-AO144-18, TDZD-8, SB216763 and SB415286. Other inhibitors are known and useful in the invention. In addition, the structure of the active site of GSK3-β has been characterised and key residues that interact with specific and non-specific inhibitors have been identified (Bertrand et al. 2003). This structural characterisation allows additional GSK inhibitors to be readily identified.

In a particular embodiment, the GSK3 inhibitor is the 6-(2-(4-(2,4-dichlorophenyl)-5-(4-methyl-1H-imidazol-2-yl)pyrimidin-2-ylamino)ethylamino)nicotinonitrile (CHIR99021) having the following formula:

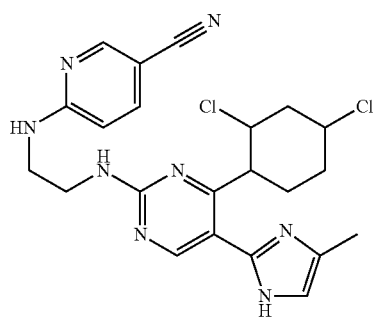 [SMILES: Cc1c[nH]c(-c2cnc(NCCNc3ccc(C#N)cn3)nc2C2CCC(Cl)CC2Cl)n1]

In another particular embodiment, the GSK3 inhibitor is a 2,6,9-trisubstituted purine as described in Zhang et al. 2007.

In a particular embodiment, the 2,6,9-trisubstituted purine is the (S)-2-(9-(biphenyl-4-ylmethyl)-2-(2,3-dihydro-1H-inden-5-yloxy)-9H-purin-6-ylamino)-3-phenylpropan-1-ol (QS11) having the following formula:

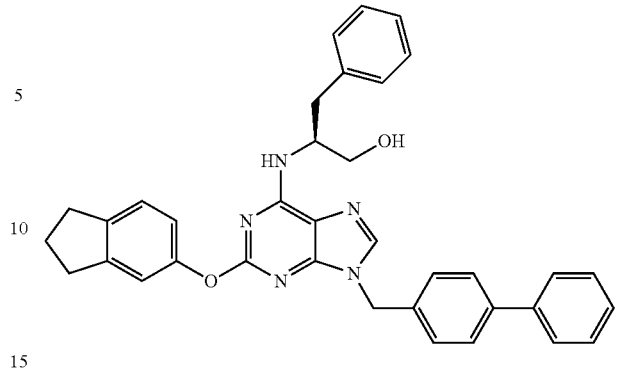

In another particular embodiment, the GSK3 inhibitor is a benzo[e]isoindole-1,3-dione as described in Zhong et al. 2009.

In a particular embodiment, the benzo[e]isoindole-1,3-dione is the 5-ethyl-7,8-dimethoxy-1H-pyrrolo[3,4-c]-isoquino line-1,3-(2H)-dione (3F8) having the following formula:

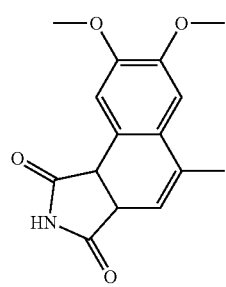 [SMILES: COc1cc2c(cc1OC)C1C(=O)NC(=O)C1C=C2C]

Alternatively, biological or chemical compounds activating expression of a Myc family gene and a Klf family gene may be used for inducing extended self-renewal of functionally differentiated somatic cells. In a particular embodiment, such biological or chemical compounds induce expression of c-Myc and Klf4 genes.

Accordingly, an activator of the signal transducer and activator of transcription 3 (STAT3) may be used in order to enhance Klf4 expression as described in Hall et al. 2009. One example of an activator of STAT3 is the cytokine leukaemia inhibitory factor (LIF).

Another aspect of the invention relates to the use of a Myc family member (gene or protein) and a Klf family member (gene or protein) for inducing extended self-renewal of functionally differentiated somatic cells.

In a particular embodiment, the Myc family member is c-Myc and the Klf family member is Klf4.

In another particular embodiment, the Myc family gene is c-Myc and the Klf family gene is Klf2.

In another particular embodiment, the Myc family gene is c-Myc and the Klf family gene is Klf5.

In another particular embodiment, the Myc family gene is N-Myc and the Klf family gene is Klf4.

In another particular embodiment, the Myc family gene is N-Myc and the Klf family gene is Klf2.

In still another particular embodiment, the Myc family gene is N-Myc and the Klf family gene is Klf5.

As previously mentioned, the Klf family gene for which the expression is activated may be chosen depending on the related functionally differentiated somatic cells.

Another aspect of the invention relates to a combination of a Myc family member (gene or protein) and a Klf family member (gene or protein) for use in a method for inducing extended self-renewal of functionally differentiated somatic cells.

In a particular embodiment, the Myc family member is c-Myc and the Klf family member is Klf4.

In another particular embodiment, the Myc family gene is c-Myc and the Klf family gene is Klf2.

In another particular embodiment, the Myc family gene is c-Myc and the Klf family gene is Klf5.

In another particular embodiment, the Myc family gene is N-Myc and the Klf family gene is Klf4.

In another particular embodiment, the Myc family gene is N-Myc and the Klf family gene is Klf2.

In still another particular embodiment, the Myc family gene is N-Myc and the Klf family gene is Klf5.

As previously mentioned, the Klf family gene for which the expression is activated may be chosen depending on the related functionally differentiated somatic cells.

Another aspect of the invention relates to a kit comprising a Myc family member (gene or protein) and a Klf family member (gene or protein) for use in a method for inducing extended self-renewal of functionally differentiated somatic cells.

In a particular embodiment, the Myc family member is c-Myc and the Klf family member is Klf4.

In another particular embodiment, the Myc family gene is c-Myc and the Klf family gene is Klf2.

In another particular embodiment, the Myc family gene is c-Myc and the Klf family gene is Klf5.

In another particular embodiment, the Myc family gene is N-Myc and the Klf family gene is Klf4.

In another particular embodiment, the Myc family gene is N-Myc and the Klf family gene is Klf2.

In still another particular embodiment, the Myc family gene is N-Myc and the Klf family gene is Klf5.

As previously mentioned, the Klf family gene for which the expression is activated may be chosen depending on the related functionally differentiated somatic cells.

A further object of the invention relates to a population of functionally differentiated somatic cells that is obtainable according to the methods of the invention.

A further object of the invention relates to a population of functionally differentiated somatic cells obtained according to the methods of the invention.

Functionally differentiated somatic cells obtained according to methods of the invention can be easily and effectively generated in vitro. The ability to obtain a large number of in vitro functionally differentiated somatic cells opens new opportunities for the therapeutic field. It should be further noted that as previously mentioned, despite the fact that c-Myc and Klf4 are both oncogenes, said in vitro functionally differentiated somatic cells are not tumorigenic in mice as analysed up to 6 months after transplantation.

Moreover, functionally differentiated somatic cells of the invention may be further genetically engineered so that said cells express a therapeutic nucleic acid of interest, which encodes a protein of interest. Suitable genes of interest include growth factors.

For instance, cells of the invention may be genetically engineered to produce gene products beneficial upon transplantation of the genetically engineered cells to a subject. Such gene products include, but are not limited to, anti-inflammatory factors, e.g., anti-TNF, anti-IL-1, anti-II-6, anti-IL-2 . . . etc.

Moreover amplified, functionally differentiated somatic cells form a patient with a genetic disease may be used for pharmaceutical screening in order to identify drugs useful for treating or alleviating disease symptoms.

Functionally differentiated somatic cells of the invention may also be further genetically engineered so that said cells correct a genetic defect before retransplantation.

Alternatively, functionally differentiated somatic cells of the invention such as macrophages may be fused to other functionally differentiated somatic cells to correct genetic defects in the target cell or to deliver therapeutic compounds.

Indeed, macrophages have been shown to fuse with cardiac muscle cells or hepatocytes and may correct a genetic defect in these cells as described in Camargo et al., 2003; Camargo et al., 2004 and Willenbring et al., 2004. For example, cells of the invention such as macrophages may therefore be also engineered to express multiple or single copies of normal or hyperactive variants of genes that are mutated in genetic disorders. Examples include but are not limited to enzyme deficiencies in the liver or dystrophin in Duchenne muscular dystrophy.

Therefore, the invention also relates to the use of an amplified functionally differentiated somatic cell, in particular a macrophage, to fuse with a target cell in vivo after transplantation.

In a particular embodiment, the fused cell according to the invention is a cell issued from the fusion of a macrophage obtained form a patient affected by Duchenne muscular dystrophy and genetically modified to express wild-type (WT) dystrophin with skeletal muscle cells form the same patient after transplantation.

The invention thus provides a pharmaceutical composition comprising functionally differentiated somatic cells as defined above, in combination with a pharmaceutically acceptable carrier or excipient. In particular embodiments, the methods of the invention provide a substantially homogeneous population of functionally differentiated somatic cells. The term "substantially homogeneous population", as used herein, refers to a population of cells wherein the majority (e.g., at least about 80%, preferably at least about 90%, more preferably at least about 95%) of the total number of cells have the specific characteristics of the fully differentiated somatic cells of interest. As used herein, the term "pharmaceutically acceptable carrier or excipient" refers to a carrier medium which does not interfere with the effectiveness of the biological activity of the functionally differentiated somatic cells of the invention, and which is not excessively toxic to the host at the concentrations at which it is administered. Examples of suitable pharmaceutically acceptable carriers or excipients include, but are not limited to, water, salt solution (e.g., Ringer's solution), alcohols, oils, gelatins, carbohydrates (e.g., lactose, amylase or starch), fatty acid esters, hydroxymethylcellulose, and polyvinyl pyrroline. Pharmaceutical compositions may be formulated as liquids, semi-liquids (e.g., gels) or solids (e.g., matrix, lattices, scaffolds, and the like). If desired, the pharmaceutical composition may be sterilized.

In certain embodiments, a pharmaceutical composition may further comprise at least one biologically active substance or bioactive factor. As used herein, the term "biologically active substance or bioactive factor" refers to any molecule or compound whose presence in a pharmaceutical composition of the invention is beneficial to the subject receiving the composition. As will be acknowledged by one skilled in the art, biologically active substances or bioactive factors suitable for use in the practice of the invention may be found in a wide variety of families of bioactive molecules and compounds. For example, a biologically active substance or bioactive factor useful in the context of the invention may be selected from anti-inflammatory agents, anti-apoptotic agents, immunosuppressive or immunomodulatory agents, antioxidants, growth factors, and drugs.

Moreover, the population of functionally differentiated somatic cells of the present invention may also have others uses. These uses include, but are not limited to, use for modelling injuries or pathologies and for screening compounds. For example said population of functionally differentiated somatic cells may also be used for a variety of in vitro and in vivo tests. In particular but in non limiting way, they find use in the evaluation of toxicity of compounds such as pharmaceutical candidate compounds.

The invention will be further illustrated by the following examples. However, these examples should not be interpreted in any way as limiting the scope of the present invention.

Example 1

Self-Renewal of Maf-DKO Macrophages and Wt Macrophages

The results reported below were presented in a scientific article (Aziz et al. 2009) which is incorporated herein by reference in its entirety.

Material & Methods:

Mice: MafB and c-Maf deficiency being lethal at or shortly after birth, we generated mice with a Maf-DKO hematopoietic system by reconstituting age- and sex-matched Ly5.1 recipients with wt or Maf-DKO E14.5 Ly5.2 fetal liver cells as described in Aziz et al. 2006.

Cells and Media: Maf-DKO macrophages were passaged every 4 days with partial medium change every 2 days in DMEM/10% FCS (Invitrogen) supplemented with 10-50 ng/ml rM-CSF (Preprotec) or 20% M-CSF containing L-929 cell conditioned IMDM/0.5% FCS medium (LCM). Colony assays were performed using Methocult-3234 (Stem Cell Technologies) supplemented with 100 ng/ml rM-CSF, IL-3 or GM-CSF (Preprotec) or Methocult-3434, containing a complete cytokine mix. Leukocytes were enriched by density gradient centrifugation using Lympholyte Mammalian® (TeBU-Biotech) after heparinized micro-capillary blood collection and red cell lysis (BD). Kupffer cells were enriched by F4/80 autoMACS™ from liver cell suspensions. FACS antibody staining was done in PBS/0.2% BSA/2 mM EDTA as described in Aziz et al. 2006. Maf-DKO macrophages ($10^7$ cells/ml) were labeled with 2.504 CFSE prior to IV injection into sub-lethally irradiated (450Gy) Ly5.1 recipients.

Assays: Cell cycle analysis was performed by BrdU-flow-cytometry® (BD) after 1 h labeling with 5 µM BrdU of cell cultures or whole blood at 37° C. Phagocytosis and NO assays were performed as described in Aziz et al. 2006 or with GFP-expressing Salmonella NPCC12023[23]. Karyotype analysis was done with KaryoMAX®Colcemid® solution (Invitrogen) and DAPI staining of metaphase chromosome spreads. RNA was isolated and quantitative RT-PCR assays were performed as described in Aziz et al. 2006. Para-formaldehyde fixed frozen tissues were stained with anti-F4/80 (Serotec; MCA497A647) or anti-Moma-1 (BMA; T-2021)/streptavidin-Alexa546 (Invitrogen; S11225) antibodies and analyzed on a Zeiss LSM510 confocal microscope. Immunoblots were done as described in Aziz et al. 2006 using anti-c-Myc (N-262; SantaCruz-764), anti-Klf4 (H-180; SantaCruz-20691) and anti-β-Tubulin-I (Sigma; T-7816) antibodies. FACS antibody staining was done in PBS/0.2% BSA/2 mM EDTA as described (Aziz et al., 2006). Cells were analyzed on FACSCalibur, FACSCanto or LSR11 and sorted on FACSAria using DIVA™ (Becton-Dickinson) or FlowJo™ software.

shRNA Viruses: shRNA sequences were determined using 'RNAi-Codex' software (http://codex.cshl.edu/scripts/newmain.pl) and cloned into LMP-GFP virus (Open Biosystems as described in Paddison et al., 2004). Maf-DKO macrophages or NIH3T3 were infected with virus produced by PhoenixE cells (www.stanford.edu/group/nolan). All error bars show standard error of the mean (SEM).

Results:

Differentiated cells can be reprogrammed into stem cells by the four transcription factors Oct-4, Sox-2, KLF4 and c-Myc, of which the latter two have been proposed to impart extended proliferation capacity based on their role in ES cell self-renewal. As KLF4 and c-Myc can also mediate monocytic differentiation and proliferation, respectively, we investigated their role in the demonstrated extended proliferative capacity of Maf-DKO macrophages (see document WO 2008/084069). We observed that relative to wt controls, Maf-DKO macrophages showed a strong up-regulation of both KLF4 and c-Myc expression but not the pluripotency factors Sox2, Oct3/4 or nanog. KLF4 and c-Myc became highly expressed within 2 h of M-CSF stimulation in M-CSF starved cells and maintained significantly higher expression levels for the observation period of 72 h.

c-Myc and KLF4 can both act as oncogenes in certain contexts as described in Rowland et al. 2006 and Adhikary et al. 2005. To determine whether the extended proliferative capacity of c-Myc and KLF4 overexpressing Maf-DKO monocytes was associated with tumorigenic transformation, we analyzed the long-term effects of MafB/cMaf deficiency in vivo. Interestingly, bone marrow chimeras with a Maf-DKO hematopoietic system showed no sign of leukaemia or myelo-proliferative disease for over one year after reconstitution. Furthermore, Maf-DKO macrophages retained a normal number of chromosomes through long-term ex vivo expansion and did not give rise to tumours upon transplantation into syngeneic or immuno-compromised nude mice, irrespective of the injection route and despite the cells' ability to divide in vivo. By comparison, under the same conditions the murine macrophage cell line J774.1 induced massive tumors within days and caused 100% mortality by 4 weeks. Rather than forming tumors, transplanted Maf-DKO macrophages showed homing to normal macrophage locations in multiple tissues. Maf-DKO cells thus contributed to macrophages of the bone marrow, peritoneum, the red pulp and marginal zone of the spleen and to Kupffer cells of the liver. Together these results indicate that expanded Maf-DKO monocytes are not transformed but subject to homeostatic control in vivo and can give rise to macrophages that integrate into the normal tissue architecture. To determine the functional consequence of these changes we generated shRNA retroviral vectors directed against KLF4 or c-Myc that could specifically reduce both endogenous and transfected target gene expression at the RNA and protein level. Maf-DKO macrophages, infected with GFP-expressing retrovirus coding for no or control shRNA sequences, gave rise to GFP$^+$ colonies in methocult assays of the same size and morphology as uninfected cells. By contrast, cells infected with GFP-retrovirus expressing either KLF4 or c-Myc shRNA gave rise to only small GFP$^+$ cell clusters of less than 20 cells that could not be propagated through serial re-plating. Internal controls of non-infected, GFP$^-$ colonies from the same plating showed identical morphology, frequency and re-plating behaviour under all conditions. Furthermore we observed that retroviral over-expression of c-Myc and KLF4 was sufficient to induce extended self-renewal capacity in wt macrophages but did not induce tumorigenic transformation. Whereas c-Myc only infected macrophage clones induced massive tumors in transplanted nude mice and resulted in the rapid death of the recipients, c-Myc/KLF4 infected macrophage clones did not, similar to MafB/c-Maf deficient macrophage clones Together, these results indicated that increased expression of both KLF-4 and c-Myc is both required and sufficient to enable extended proliferation capacity of macrophages. Our results thus indicate that long-term expansion of fully differentiated cells is possible without loss of functionality or tumorigenic transformation. Interestingly, this requires c-Myc and KLF4, which belong to a group of transcription factors that can reprogram somatic cells into pluripotent stem cells (iPS). Although not required for pluripotency c-Myc and KLF4 have been proposed to mediate extended proliferation and are important for ES cell self-renewal. The non-tumorigenicity of Maf-DKO macrophages is intriguing, given that individually both c-Myc and KLF4 can act as oncogenes as described in Rowland et al. 2006 and Adhikary et al. 2005. In particular c-Myc can malignantly transform macrophages and induce tumours in iPS derived mice. The co-expression of KLF4, however, appears to inhibit the tumorigenic potential of c-Myc, as observed in macrophages expressing both c-Myc and KLF-4 that in contrast to c-Myc only expressing macrophages were not tumorigenic. The controlled and joint up-regulation of c-Myc and KLF4 in Maf-DKO cells, however, may thus prevent malignancy by assuring a fine-tuned counter-balance of the factors' partially antagonistic activities in cell cycle control. Together our results indicate that extended amplification of fully differentiated cells can be achieved without passing through pluri- or multi-potent stem cell intermediates by a mechanism that depends on regulated activation of c-Myc and KLF4. These findings may open up new perspectives for cellular therapies in tissue regeneration.

Example 2

Self-Renewal of Wt B Lymphocytes

Material & Methods:

Cells and Media: Bone marrow from normal wild type C57/B16 mice was stimulated for 2 days in IMDM, 4% FBS, 50 ng/ml SCF, 50 ng/ml Flt3, 10 ng/ml IL6, 10 ng/ml IL7 and 140.mu. beta-mercaptoethanol and infected with empty, c-Myc only, KLF4 only or both c-Myc and KLF4 expressing retrovirus by cocultivation with supernatant from transfected pNXe packaging cell lines before plating 125,000 cells/ml in IL-7 containing Methocult-3630 (Stem Cell Technologies). After 8 days of differentiation cells were washed out from the semisolid medium and replated at 100,000 cells per ml in IL-7 containing Methocult-3630 and successively replated at various cellular concentration to facilitate counting of emerging colonies. In each case counting and replating was done after 8 days of incubation.

Assays: After the 4$^{th}$ replating all cells were washed out of the semisolid medium by repeated washed in PBS. FACS antibody staining was done in PBS/0.2% BSA/2 mM EDTA as described (Aziz et al., 2006). Cells were analyzed on FACSCalibur, FACSCanto or LSR11 and sorted on FACSAria using DIVA™ (Becton-Dickinson) or FlowJo™ software.

Results:

To investigate whether KLF-4 and c-Myc could also induce self-renewal in other cell types, we retrovirally expressed KLF-4 and c-Myc in wt B-cells. We could indeed observe that c-Myc and KLF4 enabled serial re-plating capacity of B-cells for at least 4 rounds, whereas control virus infected cells could not be replated. Similar to macrophages c-Myc only infected B-cells also gave rise to colonies initially, but could not be replated after 3 rounds, possibly due to c-Myc induced apoptosis, indicating again that the combined action of c-Myc and KLF4 is required to enable self renewal.

Example 3

Self-Renewal of Erythroid Cells

Material & Methods:

MACS depleted lineage negative cells from ROSA26-rtTA heterozygous bone marrow were maintained 24 hours in IMDM, 4% FBS, 50 ng/ml SCF, 50 ng/ml Flt3, 10 ng/ml IL11, 10 ng/ml IL7 and 140μ beta-mercaptoethanol. Then the cells were seeded at the density of 50,000 cells in a round-bottomed 96-well plate. They were infected in presence of 4 μg/ml polybrene for 24 h at MOI 40 with a concentrated lentivirus carrying doxycycline-inducible vectors expressing either Klf4 or c-Myc. Colony assays were performed in Methocult M3231 (Stem cell technology) in duplicate in presence of 1 μg/ml of doxycycline and 50 ng/ml of rEPO (Sigma) to detect erythroblasts.

Results:

To investigate whether KLF-4 and c-Myc could also induce self-renewal in other cell types, we also infected hematopoietic cells from bone marrow heterozygous for a rTA-knockin in the ROSA26 locus with inducible KLF-4 and c-Myc containing carrying doxycycline-inducible vectors expressing either Klf4 or c-Myc or a control vector. Preliminary data also indicate that combined c-Myc and KLF4 expression can also induce increased expansion of erythroid cells.

REFERENCES

Throughout this application, various references describe the state of the art to which this invention pertains. The disclosures of these references are hereby incorporated by reference into the present disclosure.

Adhikary S, Eilers M; Transcriptional regulation and transformation by Myc proteins; Nat Rev Mol Cell Biol. 2005 August; 6(8):635-45.

Aziz A, Vanhille L, Mohideen P, Kelly L M, Otto C, Bakri Y, Mossadegh N, Sarrazin S, Sieweke M H; Development of macrophages with altered actin organization in the absence of MafB; Mol Cell Biol. 2006 September; 26(18):6808-18.

Aziz A, Soucie E, Sarrazin S, Sieweke M H; MafB/c-Maf deficiency enables self-renewal of differentiated functional macrophages; Science. 2009 Nov. 6; 326(5954):867-71.

Bertrand J A, Thieffine S, Vulpetti A, Cristiani C, Valsasina B, Knapp S, Kalisz H M, Flocco M; Structural characterization of the GSK-3beta active site using selective and non-selective ATP-mimetic inhibitors; J Mol. Biol. 2003 Oct. 17; 333(2):393-407.

Camargo F D, Green R, Capetanaki Y, Jackson K A, Goodell M A; Single hematopoietic stem cells generate skeletal muscle through myeloid intermediates; Nat. Med. 2003 December; 9(12):1520-7.

Camargo F D, Finegold M, Goodell M A; Hematopoietic myelomonocytic cells are the major source of hepatocyte fusion partners; J Clin Invest. 2004 May; 113(9):1266-70.

Hall J, Guo G, Wray J, Eyres I, Nichols J, Grotewold L, Morfopoulou S, Humphreys P, Mansfield W, Walker R, Tomlinson S, Smith A; Oct4 and LIF/Stat3 additively induce Krüppel factors to sustain embryonic stem cell self-renewal; Cell Stem Cell. 2009 Dec. 4; 5(6):597-609.

Marson A, Foreman R, Chevalier B, Bilodeau S, Kahn M, Young R A, Jaenisch R; Wnt signaling promotes reprogramming of somatic cells to pluripotency; Cell Stem Cell. 2008 Aug. 7; 3(2):132-5.

Lyssiotis C A, Foreman R K, Staerk J, Garcia M, Mathur D, Markoulaki S, Hanna J, Lairson L L, Charette B D, Bouchez L C, Bollong M, Kunick C, Brinker A, Cho C Y, Schultz P G, Jaenisch R; Reprogramming of murine fibroblasts to induced pluripotent stem cells with chemical complementation of Klf4; Proc Natl Acad Sci USA. 2009 Jun. 2; 106(22):8912-7.

Paddison P J, Cleary M, Silva J M, Chang K, Sheth N, Sachidanandam R, Hannon G J; Cloning of short hairpin RNAs for gene knockdown in mammalian cells; Nat. Methods. 2004 November; 1(2):163-7.

Rowland B D, Peeper D S; KLF4, p21 and context-dependent opposing forces in cancer; Nat Rev Cancer. 2006 January; 6(1):11-23.

Wang W, Walker J R, Wang X, Tremblay M S, Lee J W, Wu X, Schultz P G; Identification of small-molecule inducers of pancreatic beta-cell expansion; Proc Natl Acad Sci USA. 2009 Feb. 3; 106(5):1427-32.

Willenbring H, Bailey A S, Foster M, Akkari Y, Dorrell C, Olson S, Finegold M, Fleming W H, Grompe M; Myelomonocytic cells are sufficient for therapeutic cell fusion in liver; Nat. Med. 2004 July; 10(7):744-8.

Zhang Q, Major M B, Takanashi S, Camp N D, Nishiya N, Peters E C, Ginsberg M H, Jian X, Randazzo P A, Schultz P G, Moon R T, Ding S; Small-molecule synergist of the Wnt/beta-catenin signaling pathway; Proc Natl Acad Sci USA. 2007 May 1; 104(18):7444-8.

Zhong H, Zou H, Semenov M V, Moshinsky D, He X, Huang H, Li S, Quan J, Yang Z, Lin S; Characterization and development of novel small-molecules inhibiting GSK3 and activating Wnt signalling; Mol. Biosyst. 2009 November; 5(11):1356-60.

The invention claimed is:

1. A method for inducing extended self-renewal of mouse or human macrophages, B lymphocytes or erythroid cells comprising a step of activating overexpression of a c-Myc gene and a Klf4 gene in said cells by transducing said cells in vitro with a retroviral vector encoding c-Myc and said Klf4 gene.

2. The method according to claim 1, wherein the retroviral vector is a lentiviral vector.

3. A population of mouse or human macrophages, B lymphocytes or erythroid cells in which extended self-renewal has been induced by an in vitro method comprising a step of activating overexpression of a c-Myc gene and a Klf4 gene in said cells by transducing said cells with a retroviral vector encoding said c-Myc gene and said Klf4 gene.

4. A pharmaceutical composition comprising a population of mouse or human macrophages, B lymphocytes or erythroid cells in which extended self-renewal has been induced by an in vitro method comprising a step of activating overexpression of a c-Myc gene and a Klf4 gene in said cells by transducing said cells with a retroviral vector encoding said c-Myc gene and said Klf4 gene;

and a pharmaceutically acceptable carrier or excipient.

5. A method for inducing extended self-renewal of mouse or human macrophages comprising a step of activating overexpression of a c-Myc gene and a Klf2 gene in said cells by transducing said cells in vitro with a retroviral vector encoding c-Myc and said Klf2 gene.

6. The method according to claim 5, wherein the retroviral vector is a lentiviral vector.

7. A population of mouse or human macrophages in which extended self-renewal has been induced by an in vitro method comprising a step of activating overexpression of a c-Myc gene and a Klf2 gene in said cells by transducing said cells with a retroviral vector encoding said c-Myc gene and said Klf2 gene.

8. A pharmaceutical composition comprising a population of mouse or human macrophages in which extended self-renewal has been induced by an in vitro method comprising a step of activating overexpression of a c-Myc gene and a Klf2 gene in said cells by transducing said cells with a retroviral vector encoding said c-Myc gene and said Klf2 gene;

and a pharmaceutically acceptable carrier or excipient.

* * * * *